(12) United States Patent
Li et al.

(10) Patent No.: US 11,279,961 B2
(45) Date of Patent: Mar. 22, 2022

(54) ASPERGILLUS ORYZAE BLCY-006 STRAIN AND APPLICATION THEREOF IN PREPARATION OF GALACTOOLIGOSACCHARIDE

(71) Applicant: SHANDONG BAILONG CHUANGYUAN BIO-TECH CO., LTD, Shandong (CN)

(72) Inventors: Fanghua Li, Shandong (CN); Zhaobo Gan, Shandong (CN); Guangpeng Dou, Shandong (CN); Xianbao Shao, Shandong (CN); Mingzhan Zhang, Shandong (CN); Qian Du, Shandong (CN); Tengteng Yang, Shandong (CN)

(73) Assignee: SHANDONG BAILONG CHUANGYUAN BIO-TECH CO., LTD, Shandong (CN)

( * ) Notice: Subject to any disclaimer, the term of this patent is extended or adjusted under 35 U.S.C. 154(b) by 0 days.

(21) Appl. No.: 17/251,125

(22) PCT Filed: Feb. 18, 2020

(86) PCT No.: PCT/CN2020/075704
§ 371 (c)(1),
(2) Date: Dec. 10, 2020

(87) PCT Pub. No.: WO2020/135893
PCT Pub. Date: Jul. 2, 2020

(65) Prior Publication Data
US 2021/0139938 A1    May 13, 2021

(30) Foreign Application Priority Data
Dec. 26, 2018   (CN) .......................... 201811596603.7

(51) Int. Cl.
*C12P 19/14*    (2006.01)
*C12N 1/14*    (2006.01)
*C12N 9/38*    (2006.01)
*C12R 1/69*    (2006.01)

(52) U.S. Cl.
CPC ................ *C12P 19/14* (2013.01); *C12N 1/14* (2013.01); *C12N 1/145* (2021.05); *C12N 9/2471* (2013.01); *C12Y 302/01023* (2013.01); *C12R 2001/69* (2021.05)

(58) Field of Classification Search
None
See application file for complete search history.

(56) References Cited

FOREIGN PATENT DOCUMENTS

| CN | 101691538 A | 4/2010 |
|---|---|---|
| CN | 103937691 A | 7/2014 |
| CN | 105112306 A | 12/2015 |
| CN | 108949713 A | 12/2018 |
| CN | 109439552 A | 3/2019 |

OTHER PUBLICATIONS

Li et al., "Breeding of Aspergillus oryzae with high yield of α-galactosidase by protoplast mutagenesis", Guangxi Journal of Light Industry, 2010, 9.
Viana et al., "Determination of Cell Permeabilization and Beta-Galactosidase Extraction from Aspergillus oryzae CCT 0977 Grown in Cheese Whey", International Journal of Chemical Engineering, 2018, vol. 2018, Article ID 1367434, 6 pages.

*Primary Examiner* — Robert J Yamasaki
(74) *Attorney, Agent, or Firm* — James S. Keddie; Bozicevic, Field & Francis LLP

(57) ABSTRACT

Provided are an *Aspergillus oryzae* BLCY-006 strain and an application thereof in the preparation of a galactooligosaccharide. The strain produces β-galactosidase, and the enzyme activity can reach 300 U/ml after culturing and fermentation, which is more than 50% higher than traditional β-galactosidase activity. The enzyme also has lactose and glucose resistance properties.

10 Claims, No Drawings

ASPERGILLUS ORYZAE BLCY-006 STRAIN AND APPLICATION THEREOF IN PREPARATION OF GALACTOOLIGOSACCHARIDE

CROSS-REFERENCE TO RELATED APPLICATIONS

This application is a § 371 national phase of International Application No. PCT/CN2020/075704, filed on Feb. 18, 2020, which claims the benefit of Chinese Application No. 201811596603.7, filed on Dec. 26, 2018, which applications are incorporated by reference herein.

TECHNICAL FIELD

The invention relates to an *Aspergillus oryzae* BLCY-006 strain and use thereof in the production of galactooligosaccharides, belonging to the technical field of microorganisms.

BACKGROUND ART

*Aspergillus oryzae* is classified in subphylum Deuteromycetes, class Hyphomycetes, order Hyphomycetales, family Moniliaceae. As a common species of *Aspergillus* fungi, it is widely distributed, mainly in food, fermented food, decayed organic matter and soil. *Aspergillus oryzae* is the production strain of traditional brewed food sauce and soy sauce in China, and can also be used to produce amylase, protease, pectinase and Kojic acid.

Galactooligosaccharides (GOS) are a group of functional oligosaccharides whose molecular structures generally comprise a galactose molecule or a glucose molecule connected with 1 to 7 galactosyl groups. In the nature, there are trace amounts of GOS in animal milk, while human breast milk contains more GOS. The establishment of the *Bifidobacterium* flora in infants is largely dependent on the GOS components in breast milk. Galactooligosaccharides have strong acid resistance and heat resistance. They cannot be digested or absorbed by human small intestine, yet they can be fermented by colonic flora. Besides, galactooligosaccharides have the effect of simultaneous proliferation of bifidobacteria and lactic acid bacteria in intestine, and can inhibit the growth of harmful pathogenic bacteria and spoilage bacteria. In addition, galactooligosaccharides are not utilized by oral bacteria such as *Streptococcus mutans*, and thus can reduce the incidence of dental caries. Galactooligosaccharides can also promote the absorption of calcium, magnesium and potassium, reduce the absorption of sodium, lower total cholesterol and triglyceride levels, improve lipid metabolism, as well as effectively stimulate intestinal peristalsis, reduce and prevent the occurrence of constipation, regulate intestinal microecology and promote intestinal health. The safety of Galactooligosaccharides have been widely recognized. In 2010, Galactooligosaccharides became the second largest functional oligosaccharide product in Japan. In September 2008, China included it in the new resource food catalog.

The current methods for producing galactooligosaccharides are mainly bacterial fermentation method and enzymatic conversion method. Bacterial fermentation method refers to the direct fermentation of lactose solution with β-galactosidase-producing strains to produce galactooligosaccharides. The disadvantage of this method is that the purity of the Galactooligosaccharides produced is not high, and the subsequent purification is difficult. Enzyme conversion method refers to a method of firstly cultivating enzyme-producing bacteria, and then extracting β-galactosidase to perform enzymatic conversion to produce galactooligosaccharides. The current problem of this method is that the activity of the extracted enzyme is low, and the conversion process is subject to the influence of the high content of the reaction by-product glucose, resulting in low conversion rate and high production cost.

Chinese patent publication CN101691538A discloses a method for preparing high-purity galactooligosaccharides, comprising *Aspergillus oryzae* fermentation, and product separation and purification steps such as ceramic membrane ultrafiltration and nanofiltration separation, in which the *Aspergillus oryzae* isolated from the soil is used as the starting strain, and the *Aspergillus oryzae* BLB-21 (Accession Number: CGMCC No. 2951) is obtained through mutagenesis and screening, and then the *Aspergillus oryzae* is used to directly ferment the high-concentration lactose solution. However, the patent still has problems such as low β-galactosidase activity, low purity and low yield of the prepared galactooligosaccharides.

CONTENTS OF THE INVENTION

Aiming at the deficiencies of the prior art, the present invention provides an *Aspergillus oryzae* BLCY-006 strain and use thereof in the production of galactooligosaccharides.

The invention also provides a method for culturing *Aspergillus oryzae* BLCY-006.

The technical solution of the present invention is as follows:

An *Aspergillus oryzae* BLCY-006 strain, which has an Accession number: CGMCC No. 16965, wherein said Accession number was obtained by depositing said strain on Dec. 5, 2018 in the China General Microbiological Culture Collection Center, the Institute of Microbiology, Chinese Academy of Sciences, at the address: No. 1, West Beichen Road, Chaoyang District, Beijing.

The original strain of *Aspergillus oryzae* BLCY-006 of the present invention was isolated from the soil near the galactooligosaccharides production workshop of Bailong Chuangyuan, Dezhou City, Shandong Province, China, and obtained through repeated mutagenesis and screening.

The strain is white and yellow at first, then turns yellowish brown to light greenish brown. Its conidia heads are radial with a diameter of 150 to 300 μm, and a few are loose columnar. Its conidiophore is about 2 mm. The strain can produce β-galactosidase at high yield, and the enzyme activity of this enzyme can reach 300 U/ml after culture and fermentation, which is more than 50% higher than the traditional β-galactosidase activity. At the same time, this enzyme also has the characteristics of lactose tolerance and glucose tolerance, and its application in the production of galactooligosaccharides can greatly improve the ability of converting lactose into galactooligosaccharides and significantly reduce production costs.

The method for culturing the aforementioned *Aspergillus oryzae* BLCY-006 comprises the following steps:

(1) inoculating the *Aspergillus oryzae* BLCY-006 into a solid medium, and performing an activating cultivation at a temperature of from 28° C. to 35° C. for 20 to 30 hours to obtain an activated strain;

(2) inoculating the activated strain as obtained in step (1) into a seed culture medium, and performing proliferating cultivation at a temperature of from 28° C. to 35° C. for 20 to 30 hours to prepare a seed broth;

(3) inoculating the seed broth as prepared in step (2) into a fermentation medium at a volume percentage of 2% to 10%, and performing an expanding cultivation at a temperature of from 28° C. to 35° C. for 25 to 35 hours to obtain a bacterial fermentation broth.

According to a preferred embodiment of the present invention, the seed culture medium in step (2) has components as follows, in terms of percentages by weight:

ammonium nitrate 0.2%, ammonium sulfate 0.1%, potassium dihydrogen phosphate 0.1%, urea 0.05%, peptone 1%, sucrose 2%, glucose 5%, balance water, pH 4.5 to 6.5.

According to a preferred embodiment of the present invention, the fermentation medium in step (3) has components as follows, in terms of percentages by weight:

sucrose 5%, glucose 5%, peptone 1%, ammonium sulfate 0.1%, potassium dihydrogen phosphate 0.1%, balance water.

According to a preferred embodiment of the present invention, the solid medium in step (1) is a conventional PDA solid medium in the art.

The use of the aforementioned *Aspergillus oryzae* BLCY-006 in the production of galactooligosaccharides, characterized by comprising the following steps:

(a) preparing a bacterial fermentation broth according to the above method for culturing the *Aspergillus oryzae* BLCY-006, and collecting the bacterial cells by filtration;

(b) adding the bacterial cells as collected in step (a) to a pre-cooled phosphate buffer and then having them react with a pre-treated adsorbent for a reaction time of 5 to 25 hours so that the bacterial cells are fixed on a surface of the adsorbent to obtain a β-galactosidase;

(c) preparing a lactose solution with a mass concentration of 40% to 60%, and adding the β-galactosidase obtained in step (b) to the lactose solution, and performing an incubating reaction for 12 hours to prepare a crude galactooligosaccharides solution;

(d) subjecting the crude galactooligosaccharides solution as prepared in step (c) to decolorization, filtration, ion exchange, chromatographic separation, concentration and drying, and galactooligosaccharides were obtained.

According to a preferred embodiment of the present invention, in step (a), the filtration is carried out by adopting a plate and frame filter-press at a working pressure of 0.3 to 0.5 MPa, and a flow rate of 5 to 10 m$^3$/h.

According to a preferred embodiment of the present invention, in step (b), the adsorbent is selected from alumina, diatomaceous earth, porous ceramics or cellulose.

According to a preferred embodiment of the present invention, in step (c), the β-galactosidase is added in an amount of 0.1 to 10 wt % based on the mass of lactose.

According to a preferred embodiment of the present invention, in step (c), the incubating reaction is carried out at a temperature of 30° C. to 60° C.

According to a preferred embodiment of the present invention, in step (d), the decolorization is carried out by adding an activated carbon in an amount of 0.1 wt % and the decolorization is performed for 1.5 hours; the chromatographic separation is carried out at an operating pressure of 0.2 MPa, a temperature of 60° C., a water consumption ratio of 1:1.2, and a feed rate of 1.8 m$^3$ per hour.

The experimental procedures not described in detail in the present invention can be carried out in accordance with the literature or the prior art.

In some aspects, there is provided a β-galactosidase, comprising an adsorbent and an enzyme-containing *Aspergillus oryzae* immobilized on the adsorbent, and the enzyme-containing *Aspergillus oryzae* is prepared from *Aspergillus oryzae* BLCY-006.

Beneficial Effect

1. In the present invention, an *Aspergillus oryzae* is isolated from soil, and a strain with high-yield of β-galactosidase is finally obtained after mutagenesis treatment techniques such as UV mutagenesis, ion implantation mutagenesis treatment and named as BLCY-006. It shows an enzyme activity of up to 300 U/ml, which is more than 50% higher than the activity of traditional β-galactosidase. At the same time, the enzyme also has the characteristics of resistance to glucose and lactose. When it is applied in the production of galactooligosaccharides, the ability of converting lactose into galactooligosaccharides can be greatly improved, and production costs can be significantly reduced.

2. In the present invention, a β-galactosidase is obtained, the use efficiency of the enzyme is improved, the degree of utilization of lactose is significantly improved, and the content of galactooligosaccharides in the crude galactooligosaccharide solution is also significantly increased, which could extremely reduce the difficulty and cost of subsequent Galactooligosaccharides purification, and significantly improve the quality of the finished galactooligosaccharides product.

SPECIFIC MODELS FOR CARRYING OUT THE INVENTION

The technical solutions of the present invention will be further described below in conjunction with examples, but the protection scope of the present invention is not limited thereto.

The materials and reagents involved in the present invention were all common commercial products.

Method for determining enzyme activity of β-galactosidase:

0.1 g of o-nitrophenol-β-D-galactopyranoside (ONPG) substrate is accurately weighed, and dissolved in 40 mL of Na$_2$HPO$_4$-citrate buffer (pH5.2, 0.1 mol/L), that was, an ONPG solution with a concentration of 0.25% (W/V). A fermentation broth to be tested is diluted to a suitable multiple by using pH5.2, 0.1 mol/L Na$_2$HPO$_4$-citric acid buffer, 800 μl of the substrate solution is pipetted and added into the test tube, pre-heated in a 60° C. water bath for 2 min, added with 200 μl of the diluted enzyme solution and mixed well, reacted for 15 min and subsequently added with 2 ml of 1 mol/L Na$_2$CO$_3$ solution to quench the reaction. The light absorption value at 420 nm (OD420) was measured. Na$_2$HPO$_4$-citrate buffer (concentration of 0.1 mol/L, pH5.2) is used as a blank control, the standard curve method is used to calculate the amount of o-nitrophenol (ONP) produced in the reaction, and then to calculate the enzyme activity of β-galactosidase.

Definition of enzyme activity unit: One unit (1U) of β-galactosidase activity referred to an amount of enzyme required to generate 1 mol of o-nitrophenol (ONP) per minute by catalyzing the substrate o-nitrophenol-β-D-galactopyranoside (ONPG) at 60° C. and pH 5.2.

Biomaterials:

An *Aspergillus oryzae* BLCY-006 strain, which has an Accession number: CGMCC No. 16965, wherein said Accession number was obtained by depositing said strain on Dec. 5, 2018 in the China General Microbiological Culture Collection Center, the Institute of Microbiology, Chinese Academy of Sciences, at the address: No. 1, West Beichen Road, Chaoyang District, Beijing.

EXAMPLE 1

The process for screening *Aspergillus oryzae* BLCY-006 was as follows:

(1) Enrichment Culture

The soil near the the Galactooligosaccharides Production Workshop of Bailong Chuangyuan, Dezhou City, Shandong Province, was selected, and the topsoil was removed with a small shovel; about 10 g of the soil was taken in a depth of 5 to 15 cm from the ground, diluted 10 times with sterile water, added to a PDA medium for enrichment culture, in which the medium had composition as follows:

200 g of potato, 20 g of glucose, 15 g to 20 g of agar, 1000 ml of deionized water, 0.2% ammonium nitrate; 0.1% ammonium sulfate; 0.1% dipotassium hydrogen phosphate; pH 6.5 to 7.0.

The method for preparing the culture medium was as follows:

200 g of potato was cut into small pieces, added with water and boiled (boiled for 20 to 30 minutes, until the potato could be pierced by a glass rod), filtered with eight layers of gauze, heated, and then added with 1 g to 10 g of agar, 0.2% ammonium nitrate, 0.1% ammonium sulfate, 0.1% dipotassium hydrogen phosphate according to actual experiment needs; continuously heated and stirred to mix evenly. After the agar was completely dissolved, glucose was added, stirred evenly, cooled down and then added with deionized water to reach 1000 ml, subpackaged into test tubes or conical flasks, stoppered, bandaged, and sterilized (121° C.) for about 20 minutes; then the test tubes were taken out and put on a slope or shaken well, and stored for later use after cooling.

(2) Separation of Pure Strain

In this step the streaking method was used. A large test tube containing 5 ml of sterile water was taken, 2 ml of the bacterial solution after the enrichment culture in step (1) was taken and added to the test tube and diluted, shaken thoroughly for dispersion, a loop of the diluted solution was aseptically picked up by using an inoculation loop and subjected to the first parallel streaking of 3 to 4 streaks on one side of a plate medium; then the petri dish was turned about 60 degrees, the remainder on the inoculation loop was burned off. After cooling, the second streaking was carried out by the method same as that of the first streaking; and the third and fourth streaking were carried out in sequence by the same method. After streaking, the petri dish was covered with a lid, turned upside down, and incubated at a temperature of from 28° C. to 35° C. for 30 hours, then single colony was picked up and inoculated on 10 slant culture media to obtain 10 slant seeds, numbered 01 to 10.

The 01 to 10 slant seeds were separately inoculated into shake flask medium and cultured at a temperature of from 28° C. to 35° C. for 30 hours. The β-galactosidase enzyme activities of the 01 to 10 shake flask fermentation broths were measured, in which the enzyme activity of the 08 shake flask was the highest, reaching 105 U/ml.

The composition of the plate medium was as follows:

200 g of potato, 20 g of glucose, 15 g to 20 g of agar, 1000 ml of deionized water, 0.2% ammonium nitrate; 0.1% ammonium sulfate; 0.1% dipotassium hydrogen phosphate; pH 6.5 to 7.0.

The composition of the shake flask medium was as follows:

100 ml of leaching juice of soybean cake, added with 2 g of soluble starch, 0.1 g of potassium dihydrogen phosphate, 0.05 g of magnesium sulfate, 0.05 g of ammonium sulfate, and 2 g of agar, natural pH.

The method for preparing the leaching juice of soybean cake comprised: 100 g of soybean cake was added with 500 ml of water, soaked for 4 hours, boiled for 3 to 4 hours, naturally filtered with gauze, and the liquid was taken and adjusted to 5 Baume.

(3) Mutagenesis Screening

The 08 strain was subjected to ultraviolet mutagenesis. The ultraviolet mutagenesis was performed by irradiation with a 20 W ultraviolet lamp from a distance of 15 cm, and the irradiation time was 200 s. The obtained high-yield strain was subjected to ion implantation mutagenesis treatment, and finally a high-yield β-galactosidase strain was obtained, named as BLCY-006, which had an enzyme activity of 300 U/ml. The strain was white and yellow at first, then turned yellowish brown to light greenish brown. The conidia heads were radial with a diameter of 150 to 300 μm, and a few were loose columnar. The conidiophore was about 2 mm. The strain was identified as *Aspergillus oryzae*.

The aforementioned *Aspergillus oryzae* was named as BLCY-006, deposited under Accession number: CGMCC No. 16965, wherein said Accession number was obtained by depositing said strain on Dec. 5, 2018 in the China General Microbiological Culture Collection Center, the Institute of Microbiology, Chinese Academy of Sciences, at the address: No. 1, West Beichen Road, Chaoyang District, Beijing.

EXAMPLE 2

The method for culturing the *Aspergillus oryzae* BLCY-006 as described in Example 1 comprised the following steps:

(1) the *Aspergillus oryzae* BLCY-006 was taken and inoculated into a PDA medium, and an activating cultivation was performed at 30° C. for 30 hours to obtain an activated strain;

(2) the activated strain as obtained in step (1) was taken and inoculated into a seed culture medium, and a proliferating cultivation was performed at 30° C. for 30 hours to prepare a seed broth;

the composition of the seed medium was as follows:

100 ml of leaching juice of soybean cake, added with 2 g of soluble starch, 0.1 g of potassium dihydrogen phosphate, 0.05 g of magnesium sulfate, 0.05 g of ammonium sulfate, and 2 g of agar, natural pH;

the method for preparing the leaching juice of soybean cake comprised: 100 g of soybean cake was added with 500 ml of water, soaked for 4 hours, boiled for 3 to 4 hours, naturally filtered with gauze, and the liquid was taken and adjusted to 5 Baume;

(3) the seed broth as prepared in step (2) was taken and inoculated into a fermentation medium at a volume percentage of 1%, and an expanding cultivation was performed at 30° C. for 35 hours to obtain a bacterial fermentation broth;

the fermentation medium had components as follows, in terms of percentages by weight:

sucrose 10%, bran 2%, yeast extract 1%, sodium nitrate 0.3%, $MgSO_4 \cdot 7H_2O$ 0.05%, balance water.

EXAMPLE 3

The method for culturing the *Aspergillus oryzae* BLCY-006 as described in Example 1 comprised the following steps:

(1) the *Aspergillus oryzae* BLCY-006 was taken and inoculated into a PDA medium, and an activating cultivation was performed at 35° C. for 20 hours to obtain an activated strain;

(2) the activated strain as obtained in step (1) was taken and inoculated into a seed culture medium, and a proliferating cultivation was performed at 35° C. for 20 hours to prepare a seed broth;

the composition of the seed medium was as follows:

100 ml of leaching juice of soybean cake, added with 2 g of soluble starch, 0.1 g of potassium dihydrogen phosphate, 0.05 g of magnesium sulfate, 0.05 g of ammonium sulfate, and 2 g of agar, natural pH;

the method for preparing the leaching juice of soybean cake comprised: 100 g of soybean cake was added with 500 ml of water, soaked for 4 hours, boiled for 3 to 4 hours, naturally filtered with gauze, and the liquid was taken and adjusted to 5 Baume;

(3) the seed broth as prepared in step (2) was taken and inoculated into a fermentation medium at a volume percentage of 10%, and an expanding cultivation was performed at 38° C. for 20 hours to obtain a bacterial fermentation broth;

the fermentation medium had components as follows, in terms of percentages by weight:

sucrose 10%, bran 2%, yeast extract 1%, sodium nitrate 0.3%, $MgSO_4.7H_2O$ 0.05%, balance water.

EXAMPLE 4

The method for culturing the *Aspergillus oryzae* BLCY-006 as described in Example 1 comprised the following steps:

(1) the *Aspergillus oryzae* BLCY-006 was taken and inoculated into a PDA medium, and an activating cultivation was performed at 32° C. for 25 hours to obtain an activated strain;

(2) the activated strain as obtained in step (1) was taken and inoculated into a seed culture medium, and a proliferating cultivation was performed at 32° C. for 25 hours to prepare a seed broth;

the composition of the seed medium was as follows:

100 ml of leaching juice of soybean cake, added with 2 g of soluble starch, 0.1 g of potassium dihydrogen phosphate, 0.05 g of magnesium sulfate, 0.05 g of ammonium sulfate, and 2 g of agar, natural pH;

the method for preparing the leaching juice of soybean cake comprised: 100 g of soybean cake was added with 500 ml of water, soaked for 4 hours, boiled for 3 to 4 hours, naturally filtered with gauze, and the liquid was taken and adjusted to 5 Baume;

(3) the seed broth as prepared in step (2) was taken and inoculated into a fermentation medium at a volume percentage of 10%, and an expanding cultivation was performed at 38° C. for 20 hours to obtain a bacterial fermentation broth;

the fermentation medium had components as follows, in terms of percentages by weight:

sucrose 10%, bran 2%, yeast extract 1%, sodium nitrate 0.3%, $MgSO_4.7H_2O$ 0.05%, balance water.

COMPARATIVE EXAMPLE 1

The original strain of *Aspergillus oryzae* obtained from the soil, but not yet subjected to mutagenesis and screening, was cultured, and the culture conditions were the same as those in Example 2.

COMPARATIVE EXAMPLE 2

Chinese patent application CN101691538A (application number: 200910018452.1) disclosed a method for preparing high-purity galactooligosaccharides. The *Aspergillus oryzae* BLB-21 (Accession number: CGMCC No. 2951) disclosed in the patent application was taken and cultured, and the culture conditions were the same as those in Example 2.

EXPERIMENTAL EXAMPLE 1

The bacterial fermentation broths obtained by culturing in Examples 2 to 4 and Comparative Examples 1 to 2 were taken, and the enzyme activities of β-galactosidase in these fermentation broths were detected. The results were shown in Table 1:

TABLE 1

Enzyme activity of bacterial fermentation broth

| Group | Enzyme activity of β-galactosidase |
| --- | --- |
| Example 2 | 305 U/mL |
| Example 3 | 311 U/mL |
| Example 4 | 315 U/mL |
| Comparative Example 1 | 162 U/mL |
| Comparative Example 2 | 189 U/mL |

It can be seen from the data in Table 1, when Examples 2 to 4 were compared with Comparative Examples 1 to 2, the β-galactosidase enzyme activities in the bacterial fermentation broths prepared by *Aspergillus oryzae* BLCY-006 provided by the present invention were significantly improved.

EXPERIMENTAL EXAMPLE 2

The use of *Aspergillus oryzae* BLCY-006 in the production of β-galactosidase comprised the following steps:

(a) the bacterial fermentation broths prepared in Examples 2 to 4 and Comparative Examples 1 to 2 were taken and filtered by a plate and frame filter-press at a working pressure of 0.3 to 0.5 MPa, and a flow rate of 5 to 10 $m^3/h$, and bacterial cells were collected;

(b) the bacterial cells as collected in step (a) were added to a pre-cooled phosphate buffer and then reacted with a pre-treated adsorbent for a reaction time of 15 hours so that the bacterial cells were fixed on a surface of the adsorbent to obtain β-galactosidases;

(c) lactose solutions with mass concentrations of 40% and 60% were prepared, respectively, the β-galactosidases obtained in step (b) were added to the lactose solutions at an addition amount of 5 wt % based on the mass of lactose, and an incubating reaction was performed for 12 hours to prepare crude galactooligosaccharide;

(d) the crude galactooligosaccharides solution as prepared in step (c) were subjected to decolorization, filtration, ion exchange, chromatographic separation, concentration and drying, and galactooligosaccharides were obtained.

Wherein, in step (d), the decolorization was carried out by adding an activated carbon in an amount of 0.1 wt % and the decolorization was performed for 1.5 hours; the chromatographic separation was carried out at an operating pressure of 0.2 MPa, a temperature of 60° C., a water consumption ratio of 1:1.2, and a feed rate of 1.8 $m^3$ per hour.

The crude galactooligosaccharides solution prepared in step (c) were taken and tested for glucose content, lactose content, galactose content, and Galactooligosaccharides content; the galactooligosaccharides prepared in step (d) were taken and tested for the yield of galactooligosaccharides; and the results were shown in Tables 2 to 3.

TABLE 2

Various indexes of production of Galactooligosaccharides from 40% lactose solution

| | Crude galactooligosaccharides solution | | | | Galactooligosaccharides | | |
|---|---|---|---|---|---|---|
| | Galactose content/% | Glucose content/% | Lactose content/% | Galacto-oligosaccharides content/% | Galacto-oligosaccharides purity/% | Galacto-oligosaccharides yield/% |
| Example 2 | 5.48 | 21.36 | 11.64 | 61.52 | 76.71 | 92.95 |
| Example 3 | 5.76 | 20.33 | 11.62 | 62.29 | 86.59 | 93.12 |
| Example 4 | 6.07 | 21.44 | 11.16 | 61.33 | 86.22 | 93.01 |
| Comparative Example 1 | 7.93 | 32.36 | 19.13 | 40.24 | 70.39 | 75.32 |
| Comparative Example 2 | 9.69 | 28.75 | 16.01 | 45.55 | 72.47 | 77.25 |

TABLE 3

Various indexes of production of Galactooligosaccharides from 60% lactose solution

| | Crude galactooligosaccharides solution | | | | Galactooligosaccharide | | |
|---|---|---|---|---|---|---|
| | Galactose content/% | Glucose content/% | Lactose content/% | Galacto-oligosaccharide content/% | Galacto-oligosaccharide purity/% | Galacto-oligosaccharide yield/% |
| Example 2 | 4.54 | 22.56 | 11.59 | 61.31 | 86.32 | 92.83 |
| Example 3 | 5.07 | 21.14 | 11.44 | 62.35 | 86.45 | 93.26 |
| Example 4 | 5.70 | 21.29 | 11.26 | 61.75 | 86.17 | 93.14 |
| Comparative Example 1 | 7.93 | 32.36 | 19.13 | 40.58 | 70.25 | 75.28 |
| Comparative Example 2 | 11.02 | 28.95 | 15.31 | 44.72 | 72.36 | 77.39 |

It can be seen from the above data that by using the bacterial fermentation broths prepared by *Aspergillus oryzae* BLCY-006 provided by the present invention, the degree of utilization of lactose in the crude galactooligosaccharides solution prepared in Examples 2 to 4 were not lower than 88%, the Galactooligosaccharides contents reached more than 61%; while the degree of utilization of lactose in Comparative Examples 1 to 2 were only about 81%, and the Galactooligosaccharides contents in the crude galactooligosaccharides solution were only about 40%. It could be concluded from the comparison that the using *Aspergillus oryzae* provided by the present invention for preparing galactooligosaccharides could significantly improve the degree of utilization of lactose, and the content of galactooligosaccharides in the produced crude galacto-oligosaccharide solution was also significantly increased.

From the analysis of the final galactooligosaccharides product as obtained, the galactooligosaccharides prepared in Examples 2 to 4 all had a purity of above 85%, and the galactooligosaccharides prepared in Comparative Examples 1 to 2 had a purity of not exceeding 75%. The galactooligosaccharides prepared using the bacterial fermentation broths of Examples 2 to 4 had a yield of about 92%, while the galactooligosaccharides prepared using the bacterial fermentation broths of Comparative Examples 1 to 2 had a yield of only about 75%. As compared to Comparative Examples 1 to 2, Examples 2 to 4 had significantly improved purity and yield of galactooligosaccharides.

What is claimed is:

1. An *Aspergillus oryzae* BLCY-006 strain, which has an accession number: CGMCC No. 16965, wherein said accession number was obtained by depositing said strain on Dec. 5, 2018 in the China General Microbiological Culture Collection Center, the Institute of Microbiology, Chinese Academy of Sciences, at the address: No. 1, West Beichen Road, Chaoyang District, Beijing.

2. A method for culturing the *Aspergillus oryzae* BLCY-006 according to claim 1, characterized by comprising the following steps: (1) inoculating the *Aspergillus oryzae* BLCY-006 into a solid medium, and performing an activating cultivation at a temperature of from 28° C. to 35° C. for 20 to 30 hours to obtain an activated strain; (2) inoculating the activated strain as obtained in step (1) into a seed culture medium, and performing a proliferating cultivation at a temperature of from 28° C. to 35° C. for 20 to 30 hours to prepare a seed broth; (3) inoculating the seed broth as prepared in step (2) into a fermentation medium at a volume percentage of 2% to 10%, and performing an expanding cultivation at a temperature of from 28° C. to 35° C. for 25 to 35 hours to obtain a bacterial fermentation broth.

3. The method according to claim 2, characterized in that the seed culture medium in step (2) has components as follows, in terms of percentages by weight: ammonium nitrate 0.2%, ammonium sulfate 0.1%, potassium dihydrogen phosphate 0.1%, urea 0.05%, peptone 1%, sucrose 2%, glucose 5%, balance water, pH 4.5 to 6.5.

4. The method according to claim 2, characterized in that the fermentation medium in step (3) has components as follows, in terms of percentages by weight: sucrose 5%, glucose 5%, peptone 1%, ammonium sulfate 0.1%; potassium dihydrogen phosphate 0.1%, balance water.

5. The method according to claim 2, characterized in that the solid medium in step (1) is potato dextrose agar (PDA) solid medium.

6. A method comprising the following steps:
(a) culturing *Aspergillus oryzae* BLCY-006 using the method of claim 2, and collecting bacterial cells by filtration;
(b) adding the bacterial cells as collected in step (a) to a pre-cooled phosphate buffer and then having them react with a pre-treated adsorbent for a reaction time of 5 to 25 hours so that the bacterial cells are fixed on a surface of the adsorbent to obtain a β-galactosidase;
(c) preparing a lactose solution with a mass concentration of 40% to 60%, and adding the β-galactosidase obtained in step (b) to the lactose solution, and performing an incubating reaction for 12 hours to prepare a crude galactooligosaccharides solution;
(d) subjecting the crude galactooligosaccharides solution as prepared in step (c) to decolorization, filtration, ion exchange, chromatographic separation, concentration and drying, and galactooligosaccharides were obtained.

7. The method according to claim 6, characterized in that the filtration in step (a) is carried out by adopting a plate and frame filter-press at a working pressure of 0.3 to 0.5 MPa, and a flow rate of 5 to 10 $m^3$/h.

8. The method according to claim 6, characterized in that the adsorbent in step (b) is selected from alumina, diatomaceous earth, porous ceramics or cellulose.

9. The method according to claim 6, characterized in that the amount of β-galactosidase added in step (c) is 0.1% to 10% by weight based on the mass of lactose; the temperature of the incubating reaction is 30° C. to 60° C.

10. The method according to claim 6, characterized in that the decolorization in step (d) is carried out by adding an activated carbon in an amount of 0.1 wt %, the decolorization is performed for 1.5 hours; the chromatographic separation is carried out at an operating pressure of 0.2 MPa, a temperature of 60° C., a water consumption ratio of 1:1.2, and a feed rate of 1.8 $m^3$ per hour.

* * * * *